US006661866B1

(12) United States Patent
Limkeman et al.

(10) Patent No.: US 6,661,866 B1
(45) Date of Patent: Dec. 9, 2003

(54) INTEGRATED CT-PET SYSTEM

(75) Inventors: Mark Kenneth Limkeman, Brookfield, WI (US); Alexander Ganin, Whitefish Bay, WI (US); Charles William Stearns, New Berlin, WI (US); David Leo McDaniel, Dousman, WI (US); Robert Franklin Senzig, Germantown, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/064,912

(22) Filed: Aug. 28, 2002

(51) Int. Cl.$^7$ ............................................... G01N 23/00
(52) U.S. Cl. .......................... 378/19; 250/363.04; 378/4
(58) Field of Search .................... 378/4–20; 250/363.04

(56) References Cited

U.S. PATENT DOCUMENTS

| | | |
|---|---|---|
| 5,376,795 A | 12/1994 | Hasegawa et al. |
| 5,600,145 A | 2/1997 | Plummer |
| 5,672,877 A | 9/1997 | Liebig et al. |
| 6,211,523 B1 | 4/2001 | Gagnon |

OTHER PUBLICATIONS

"Application Of Cadmiun Telluride Detector To High Speed X–Ray CT Scanner" Hori et al, Nuclear Instruments and Methods in Physics Research, A 380 1996 p. 397–401.*
A Novel APD–Based Detector Module for Multi–Modality PET/SPECT/CT Scanners, 1999 IEEE, A Saoudi & R. Lecomte.
Description of a Simultaneous Emission–Transmission CT System; SPIE/vol. 1231 Medical Imaging IV: Image Formation (1990); pp. 50–60; Bruce H. Hasegawa, et al.
Description of a Prototype Emission–Transmission Computed Tomography Imaging System; J. Nucl. Med. 1992; 33: 1881–1887; Thomas F. Lang, et al.

* cited by examiner

Primary Examiner—Craig E. Church
(74) Attorney, Agent, or Firm—Quarles & Brady, LLP; Carl Horton

(57) ABSTRACT

A combined emission-transmission imaging apparatus, the apparatus comprising oppositely facing first and second photon detector segments disposed on opposite sides of an imaging area and defining the imaging area there between and a radiation source disposed adjacent and outside the imaging area and adjacent at least one of the detector segments, the source generating a fan beam of radiation that emanates from a focal point and juxtaposed such that the fan beam is directed along a trajectory through the imaging area and toward the other of the detector segments, wherein the segments collect both emission and transmission radiation.

20 Claims, 3 Drawing Sheets

INTEGRATED CT-PET SYSTEM

BACKGROUND OF INVENTION

The field of the invention is medical imaging and more particularly medical imaging with a combined CT-PET system.

Throughout this specification, in the interest of simplifying this explanation, a clinical region of a patient to be imaged will be referred to generally as a "region of interest" and prior art and the invention will be described with respect to a hypothetical region of interest. In addition, the phrase "translation axis" will be used to refer to an axis along which a patient is translated through an imaging system during data acquisition.

The medical imaging industry has developed many different types of imaging systems that are useful for diagnostic purposes. Two of the more widely used systems include computerized tomography (CT) systems and positron emission tomography (PET) systems.

In CT systems, an X-ray-source projects a fan-shaped X-ray beam which is collimated to lie within an X-Y plane of a Cartesian coordinate system, termed the "CT imaging plane." The X-ray beam passes through a region of interest, such as the torso of a patient, and impinges upon an array of radiation detectors. The intensity of the transmitted radiation is dependent upon the attenuation of the X-ray beam by the region of interest and each detector produces a separate electrical signal that is a measurement of the beam attenuation. The attenuation measurements from all the detectors are acquired separately to produce a transmission profile. A group of X-ray attenuation measurements from the detector array at a given angle is referred to as a "view" and a "scan" of the object comprises a set of views made at different angular orientations during one revolution of the X-ray source. Using various data collection and manipulation techniques CT data can be used to generate two and three dimensional images of the region of interest.

Unlike CT systems that rely on an external X-ray source to generate image data, PET systems rely on an energy source that resides within a region of interest. To this end, positrons are positively charged electrons which are emitted by radionuclides that have been prepared using a cyclotron or other device. The radionuclides most often employed in diagnostic imaging are fluorine-18, carbon-11, nitrogen-13 and oxygen-15. Radionuclides are employed as radioactive tracers called "radiopharmaceuticals" by incorporating them into substances such as glucose or carbon dioxide.

To use a radiopharmaceutical in PET imaging, the radiopharmaceutical is administered, typically by injection, to a patient and accumulates in an organ, vessel or the like, which is to be imaged. It is known that specific radiopharmaceuticals become concentrated within certain organs and tumors or, in the case of a vessel, that specific radiopharmaceuticals will not be absorbed by a vessel wall. Thus, to image a specific region of interest, a radiopharmaceutical known to accumulate either within the region of interest, within an organ that resides in the region of interest or within a fluid that passes through the region of interest can be selected. The process of concentrating often involves processes such as glucose metabolism, fatty acid metabolism and protein synthesis.

After the radiopharmaceutical becomes concentrated within a region of interest and while the radionuclides decay, the radionuclides emit positrons. The positrons travel a very short distance before they encounter an electron and, when the positron encounters an electron, the positron is annihilated and converted into two photons, or gamma rays. This annihilation event is characterized by two features which are pertinent to medical imaging and particularly to medical imaging using positron emission tomography (PET). First, each gamma ray has an energy of essentially 511 keV upon annihilation. Second, the two gamma rays are directed in substantially opposite directions.

In PET imaging, if the general locations of annihilations can be identified in three dimensions, a three dimensional image of a region of interest can be reconstructed for observation. To detect annihilation locations, a PET camera is employed. An exemplary PET camera includes a plurality of detectors and a processor which, among other things, includes coincidence detection circuitry. Each time an approximately 511 keV positron impacts a detector, the detector generates an electronic signal or pulse which is provided to the processor coincidence circuitry.

The coincidence circuitry identifies essentially simultaneous pulse pairs which correspond to detectors which are essentially on opposite sides of the imaging area. Thus, a simultaneous pulse pair indicates that an annihilation has occurred on a straight line between an associated pair of detectors. Over an acquisition period of a few minutes millions of coincidence events are recorded, each coincidence event is associated with a unique detector pair. After an acquisition period during which coincidence data is collected from every angle about an imaging area, recorded coincidence data can be used via any of several different well known procedures to construct images of radionuclide concentration in the region of interest. In the case of PET systems, PET data can be collected simultaneously from a volume within an object of interest so that a 3D image can be generated.

As is the case in virtually all imaging systems, one measure of the value of a PET system is throughput. To this end, in a radiology department the number of images generated is generally related to profitability with greater numbers of images translating into greater profitability. Thus, PET acquisition systems are generally designed to collect required imaging data rapidly. For this reason, one well accepted PET configuration is generally referred to as a full ring system which, as its label implies, includes a plurality of detector segments arranged to form an annular detector surface about an imaging area such that the system detects annihilation photons from many angles at a time. Hereinafter, for the purposes of this explanation a full ring detector system will be assumed unless indicated otherwise.

Each of the different imaging modalities typically has uses for which it is particularly advantageous. For example, CT systems that employ X-rays are useful for generating anatomical images of bone and the like while PET systems are useful for generating functional images corresponding to dynamic occurrences such as metabolism and the like.

For various reasons, in some diagnostic applications, it is advantageous to collect both CT and PET data corresponding to the same clinical region of interest. For instance, CT data may be used to compensate for inaccuracies in PET imaging data. To this end, one of the problems with PET imaging techniques is that gamma ray absorption and scatter by portions of the region of interest between the emitting radiopharmaceutical and a detector distort collected data and hence resultant images. One solution for compensating for gamma ray attenuation is to assume uniform positron attenuation throughout the region of interest. That is, the region of interest is assumed to be completely homogenous in terms of radiation attenuation with no distinction made for bone, soft tissue, lung, etc. This assumption enables attenuation estimates to be made based on the surface contour of the region of interest. Unfortunately, typical regions of interest do not cause uniform radiation attenuation and therefore a uniform attenuation assumption is generally inaccurate.

According to several methods, instead of assuming uniform attenuation characteristics throughout the region of interest, CT transmission data is collected for the entire region of interest and is used to accurately determine attenuation characteristics at every point throughout the region of interest. Thereafter, the PET emission data is corrected as a function of the CT attenuation map to generate more accurate PET images.

As another instance where it is advantageous to generate both CT and PET data for a region of interest, sometimes it is advantageous to generate images that include both anatomical and functional characteristics. To this end, one solution has been to sequentially use separate imaging systems to gather both functional and static imaging data sets and then combine those sets or corresponding images to generate unified functional/static images. For example, a CT system may be used to generate an anatomical CT image and subsequently a PET system may be used to generate a functional PET image, the two images being combined thereafter to generate the unified image.

Unfortunately, where both CT and PET imaging data have to be acquired for a single region of interest, several configuration and processing problems have to be overcome. First, after functional and anatomical image data has been collected, there has to be some way to align the functional and anatomical images so that the unified image precisely reflects relative anatomic juxtapositions. To this end, in some cases, fiducial markers have been employed. For example, a metallic button with a positron emitter can be placed on the surface of a patient's skin Which is detectable by both the CT and PET systems. By aligning the marker in the resulting images the images can be aligned.

Second, where two separate imaging configurations are employed, a patient has to be moved from one configuration to the next between acquisition sessions. Movement increases the likelihood that the patient's positions during the two imaging sessions will change thus tending to reduce the possibility of accurate alignment (i.e., relative positions of organs or the like could change during movement). The possibility of misalignment is exacerbated by the fact that often imaging session schedules will not allow both CT and PET imaging processes to be performed during the same day. Thus, overall diagnostic value of the resulting unified image can be reduced appreciably through movement between acquisition periods.

Third, where two separate imaging systems are employed to obtain imaging data during two separate acquisition periods, the time required to acquire needed data is relatively long and hence throughput (i.e., the number of imaging sessions that can be performed over the course of a given period) is reduced.

One solution to eliminate the need to move patients between acquisition systems is to provide a dual CT-PET imaging system. To this end, one general type of dual imaging system includes, in effect, a CT system mounting in some fashion to a PET system so that data is sequentially collected for the region of interest, first the PET or CT data and then, after table and region of interest translation along a translation axis, the CT or PET data. These types of systems are better than two separate acquisition systems because they generally minimize patient movement and therefore facilitate data alignment.

While better than separate acquisition systems, these dual systems have several shortcomings such as bore or imaging area length as each of the adjacent system requires its own imaging area. In addition to requiring additional space, long bore length often increases patient discomfort as such systems are generally psychologically intimidating (i.e., many patients become nervous when placed in a long bore) and often result in additional patient movement. Moreover, these dual systems require two separate detector assemblies, one for CT and one for PET data acquisition. Furthermore, these types of systems still require two separate and sequential imaging periods to collect data.

One other solution to eliminate patient movement while still enabling acquisition of both CT and PET data has been to provide a radiation transmission source within the imaging area between facing PET detectors that transmits radiation toward one of the PET detectors. One exemplary system (hereinafter "the Saoudi system") of this type has been described in an article entitled "A Novel APD-Based Detector Module for Multi-Modality PET/SPECT/CT Scanners" by A. Saoudi and R. Lecomte that was published in the IEEE 1999 publication. The Saoudi system including a full ring detector constructed to receive and differentiate both emission and transmission data and a transmission X-ray source. The X-ray source is positioned inside the ring detector, presumably on a track of some type, for rotation about the internal surface of the detector to direct a fan beam across an imaging area within the detector bore.

To operate the Saoudi system, after a radionuclide has accumulated within an organ that resides in a region of interest, a patient is positioned on a support table with the region of interest inside the imaging area. Thereafter the transmission source is turned on to direct the fan beam across the imaging area through the region of interest and toward a portion of the detector on the opposite side of the imaging area. The section of the detector subtended by X-rays from the transmission source acquires both annihilation photons from the radionuclide and also transmitted X-rays from the source while other sections of the detector that are not subtended by the X-rays collect only annihilation photon data. The source is rotated about the imaging area during a data acquisition process so that transmission data is collected from every angle about the imaging area. Sorting circuitry differentiates between the different energies of the annihilation photons and the X-rays and thus two separate sets of data, an emission set and a transmission set, are acquired.

The Saoudi system is better than the previous solutions but also has several disadvantages. First, when the source is between a detector segment and the concentrated radionuclide (i.e., the organ being imaged), the source blocks emission data from reaching the detector segment and some of the PET data is lost which either results in a less accurate image or increases the time necessary to collect required PET data.

Second, because Saoudi teaches placement of the fan beam X-ray source inside the detector and essentially inside the imaging area, the size of the imaging area has to be increased to accommodate a patient and still provide sufficient space for the source to rotate therein between the patient and the detector. A larger imaging are also requires a larger full ring detector which increases costs appreciably.

U.S. Pat. No. 5,600,145 (hereinafter "the '145 patent") which issued on Feb. 4, 1997 and is entitled "Emission/

Transmission Device for use with a Dual Head Nuclear Medicine Gamma Camera with the Transmission Source Located Behind the Emission Collimator" describes one attempt to reduce the size of a combined CT-PET system. To this end, the '145 patent system teaches opposing first and second emission/transmission detectors and a line transmission source having a length that is substantially similar to the length of the first detector. The line source is mounted between the first detector and a collimator corresponding to the first detector so that the source generates a line of radiation directed across an imaging area between the first and second detectors and toward the second detector with the source length traversing across the first detector length and for movement across a first detector width perpendicular to the detector length.

In operation, after a radiopharmaceutical has accumulated in an organ that is within a region of interest, the region of interest is positioned between the detectors, the line source is turned on and is moved across the width of the first detector and the second detector collects both emission and transmission data corresponding to the radiopharmaceutical and the source, respectively while the portion of the first detector that is not blocked by the source collects emission data. The detectors (including the X-ray source) are rotated about the region of interest to collect data from all angles and, after acquisition, a sorter sorts the data by energy levels into emission and transmission data.

Here, the '145 patent teaches that by placing the line source between the detector surface and the detector collimator the distance between the emitting positron source and the detector surface can be minimized as there is no need for an additional collimator for the line source. Nevertheless, the line source, like the source in the Saoudi reference, increases the positron source-detector distance. In addition, it is unclear how the teachings of the '145 patent could be applied in the case of a full ring detector to expedite emission data acquisition.

SUMMARY OF INVENTION

It has been recognized that, where a PET detector assembly includes first and second detector segments on opposite sides of an imaging area, an X-ray source can be placed outside the imaging area and adjacent one of the detector segments where the source generates an X-ray directed across the imaging area and toward the other segment of the detector such that the detector assembly and the source can be used to essentially simultaneously collect both transmission and emission data thereby overcoming many of the problems discussed above.

Consistent with the above description, the invention includes a photon imaging apparatus comprising oppositely facing first and second emission/transmission detector segments disposed on opposite sides of an imaging area and defining the imaging area there between and a radiation source disposed adjacent and outside the imaging area and adjacent at least one of the detector segments, the source generating a fan beam of radiation that emanates from a focal point and juxtaposed such that the fan beam is directed along a trajectory through the imaging area and toward the other of the detector segments, wherein the segments collect both emission and transmission radiation.

The invention also includes a method for collecting both emission and transmission imaging data, sequentially or concurrently, corresponding to a region of interest within a patient where a radiopharmaceutical has accumulated within the region of interest and is generating emission radiation. The method comprises the steps of placing the region of interest within an imaging area between first and second photon detector segments, directing a fan beam of transmission radiation from a focal spot adjacent and outside the imaging area along a trajectory through the imaging area and toward at least one of the detector segments and collecting both the emission and transmission radiation via the first and second detector segments.

Moreover, the invention also includes a combined emission-transmission imaging apparatus, the apparatus comprising a full ring photon detector assembly including detector segments that are arranged to form an annular detector surface about an imaging area and radiation source disposed adjacent and outside the imaging area and adjacent a first side of the detector assembly, the source generating a fan beam of radiation that emanates from a focal point and juxtaposed such that the fan beam is directed along a trajectory through the imaging area and toward the detector surface on an opposite side of the imaging area, the source controllable to alter the position of the focal point and hence the trajectory of the fan beam such that the fan beam is directable across the imaging area along various trajectories and toward various segments of the detector surface, wherein the segments collect both emission and transmission radiation.

To reduce patient exposure to X-rays, in at least one embodiment of the invention, a CT source collimator is provided that collimates the CT X-ray beam in a desired fashion. To this end, the collimator may include two jaws having either straight or curved collimating edges separated along the Z-axis. The collimator may be stationary or, in the alternative, may be rotated along with the point at which X-rays are generated. Where the collimator edges are straight, the resulting beam that subtends the detector will have curve to it and hence software will have to be provided to compensate for the curvature. However, where the collimator includes curved edges that are selected appropriately, the beam subtending the detector will not include curvature and less software processing will be required.

These and other objects, advantages and aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

DETAILED DESCRIPTION

Figure 1:
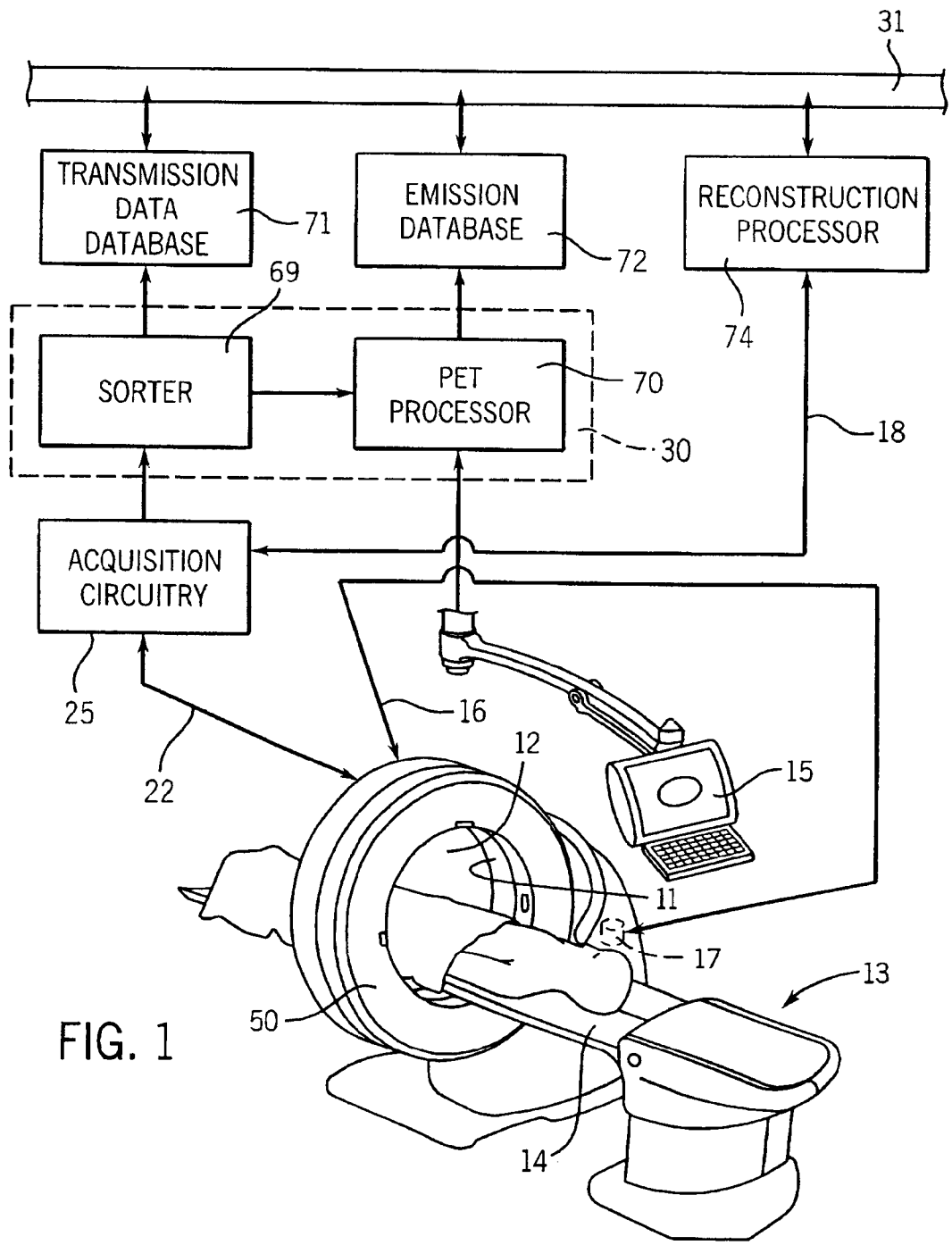
FIG. 1 is a schematic diagram illustrating a dual CT-PET imaging system according to the present invention.

Referring now to the drawings and particularly to FIG. 1, one embodiment of the inventive combined CT-PET scanner system includes a gantry 10, an annular and stationary X-ray transmission source 50, an operator work station 15, a patient support and translating table 13 and various processors, sorters and databases used to acquire and manipulate emission and transmission data. The various processors, sorters and databases will be described in more detail below. Gantry 10 supports a full ring annular detector assembly 11 about a central opening or bore 12 which is also referred to herein as an imaging area. A patient table 13 is positioned in front of the gantry 10 and is aligned with a central or translation axis of the imaging area 12. A patient table controller (not shown) moves a table bed 14 into and out of imaging area 12 in response to commands received from operator work station 15 through a communications link 16.

A gantry/detector controller 17 is mounted within the gantry 10 and is responsive to commands received from the operator work station 15 through link 16 to operate the gantry and detector ring 11. For example, the gantry can be tilted away from vertical on command from the operator, the detector can be controlled to perform a coincidence timing calibration scan to acquire corrective data, can be controlled to perform a normal "emission scan" in which positron annihilation events are counted, can be controlled to perform a transmission scan or can be controlled in any of several different manners to perform both emission and transmission acquisitions either simultaneously or in some interleaved manner as described in more detail below. Unless indicated otherwise hereafter, the invention will be described in the context of detector ring 11 being used to simultaneously collect both transmission and emission data.

The detector ring 11 is constructed using detector elements that can generate both emission and transmission data. To this end several detectors having suitable characteristics have been developed within the industry. One such detector ring has been described in the above referenced Saoudi reference (i.e., "A Novel APD-Based Detector Module for Multi-Modality PET/SPECT/CT Scanners, published in 1999 in an IEEE publication) which is incorporated herein by reference for its teachings regarding a multi-modality detector. Other multi-modality detectors are contemplated.

For the purposes of the present invention it should suffice to say that the detectors that form ring 11 are capable of identifying each of annihilation photons and transmission X-rays and generating signals that differentiate between the two detection types. To this end, the detectors forming ring 11 generally generate intensity output signals corresponding to each detected X-ray or annihilation photon where the intensities of the signals can be used to determine which detection type, emission or transmission, has occurred.

Referring still to FIG. 1, the processors, sorters and databases include acquisition circuitry 25, an acquisition processor 30, a transmission data database 71, an emission database 72 and a reconstruction processor. As well known in the art other computing components would be included with the system which have been omitted here in the interest of simplifying this explanation.

Referring still to FIG. 1, detector ring 11 provides the intensity signals to the acquisition circuitry 25 via line 22. The acquisition circuitry 25 determines the location of an event (i.e., the position on the detector ring at which an X-ray or a annihilation photon was absorbed) the time (i.e., an event detection pulse) at which an event occurs and the energy of the intensity signals corresponding to the event. The energy, time and location data is provided to acquisition processor 30 via a data bus 26.

Among other components, processor 30 includes an energy sorter 69 and a PET processor 70. Sorter 69 compares the event energies to a range of energy that includes the expected energies of X-rays passing through the region of interest. When sorter 69 identifies an X-ray event, sorter 69 updates a transmission data database 71 to indicate the location of the event on the detector. X-ray events are correlated with specific rays that are a function of the instantaneous location and trajectory of the source 50 with respect to the imaging area 12.

Generally, the location from which the source 50 generates the X-ray beam(s) and the shape (e.g., fan beam across a specific arc) and trajectory will be known and therefore the segment(s) of detector ring 11 that will potentially acquire X-ray range energy will be known. Thus, the acquisition circuitry can be programmed to only attempt to identify X-ray range energies for the detector ring segments across from the point at which a fan beam emanates. This type of limitation reduces required processing power appreciably.

When the energy corresponding to an intensity signal is above the X-ray range, sorter 69 provides the time, location and energy data to PET processor 70. Processor 70 generally uses the received data to identify pairs of data corresponding to annihilation events that occurred inside the region of interest. Any of several different algorithms known in the art can be used for this purpose. For instance, one exemplary algorithm is described in U.S. Pat. No. 5,272,343 which issued on Dec. 12, 1993 and is entitled "Sorter for Coincidence Timing Calibration in a PET Scanner" which is incorporated herein by reference for its teaching regarding the PET processor 70. It should suffice to say, in this regard, that after processor 30 identifies an annihilation event, processor 30 updates data in an emission database 72 to reflect the annihilation.

Referring still to FIG. 1, after an acquisition session has been completed and complete sets of transmission and emission data have been stored in databases 71 and 72, respectively, a reconstruction processor 74 accesses the data in databases 71 and 72 and uses the accessed data to generate whatever images are required by a system operator. The operator can use workstation 15 to select image types and views.

Figure 2:
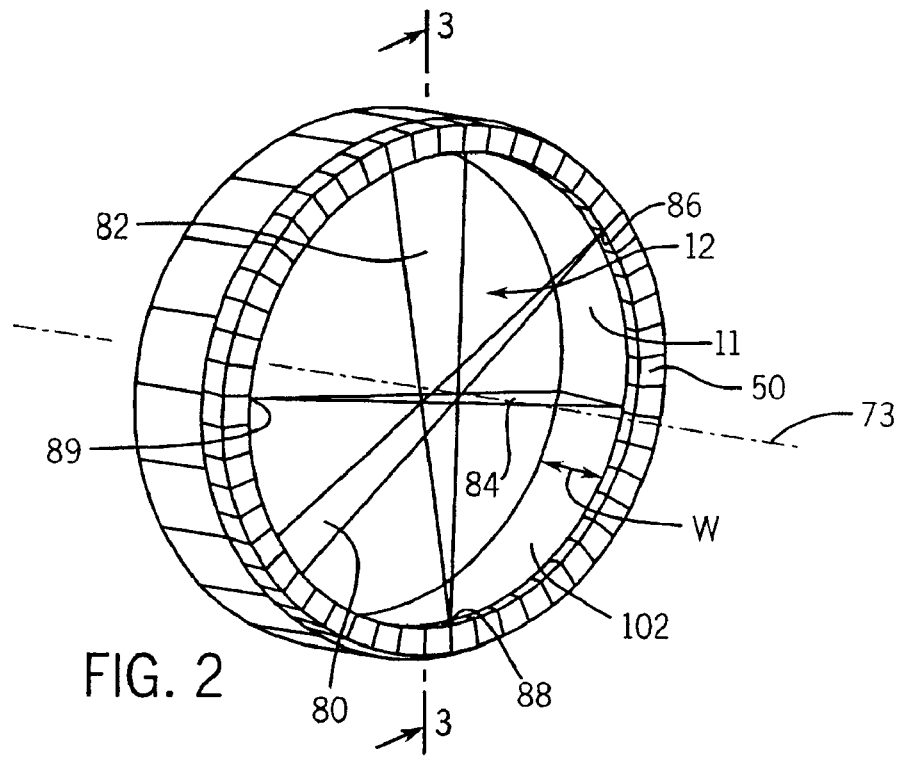
Fig. 2 is a perspective view of a detector ring and a single annular X-ray source according to the present invention.
Figure 3:
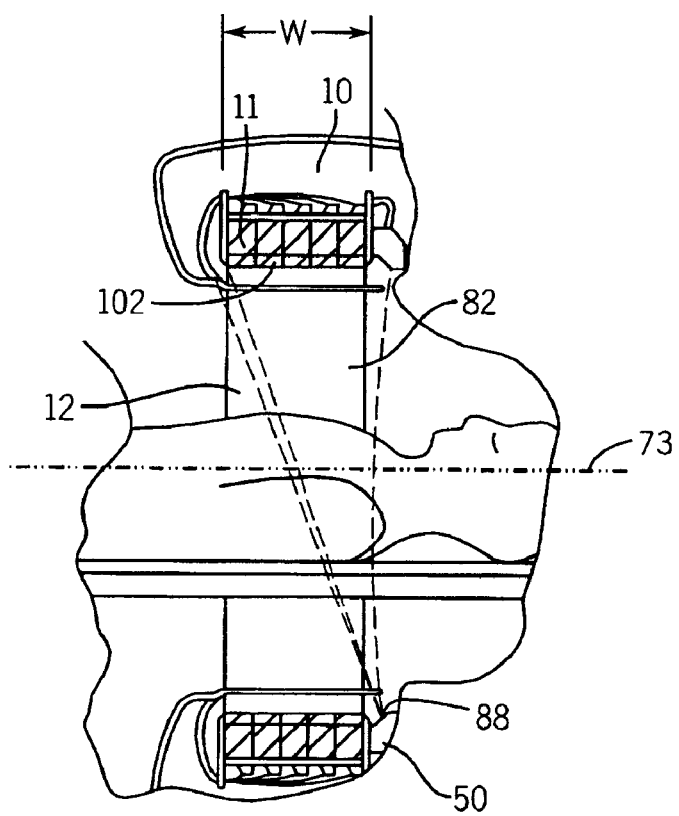
FIG. 3 is a partial cross-sectional view taken along the line 3—3 in FIG. 2, albeit with a patient on a support table positioned within an imaging area.

Referring now to FIGS. 1 through 3, source 50 is generally constructed to be able to generate a fan beam 82 of X-rays that can be directed across the imaging area 12 from virtually any angle perpendicular to a gantry or translation axis 73. In at least one embodiment, a single annular source 50 is provided which is mounted to one side of the detector ring 11. Source 50 may be restricted to generating a single fan beam 82 at a time where the fan beam 82 emanates from a single focal spot 88 and is directed toward a detector ring segment opposite the focal spot 88. In the alternative, source 50 may be configured to be able to generate several (e.g., 3–5) separate fan beams 80, 82, 84, etc. (see FIG. 2) that emanate from different focal spots 86, 88, 89, etc., respectively, simultaneously. In this case the beam trajectories must be selected such that they do not overlap so that the source of detected X-rays is known.

While various source types are contemplated, in at least one embodiment a solidstate ring type source 50 may be employed. U.S. Pat. application Ser. No. 09/751,110 which was filed on Dec. 29, 2000, is entitled "Solid-State CT System And Method" (hereinafter "the solid-state source reference") and is commonly owned with the present invention teaches one such solid-state ring type source. The solid-state source reference is incorporated herein by reference for its teachings regarding solidstate X-ray sources and specifically for teaching a continuous tube or ring type source capable of generating X-ray beams from various angles about an imaging area without requiring a large vacuum system, complicated beam deflection systems, a rotating anode target, motors, etc. For the purposes of the present invention it should suffice to say that the continuous tube may be formed in a ring as illustrated in FIG. 2 and would include an annular cathode spaced apart from an annular anode where the cathode includes a plurality of addressable (i.e., independently activated) cathode emitters. The focal spot (e.g., FIGS. 2 and 3) is selectable by addressing a specific cathode emitter which then generates a stream of electrons directed at an adjacent segment of the anode. When electrons impinge the anode X-rays are released by the anode and form the fan beam.

In FIGS. 2 and 3, generally, the fan beams 80, 82 and 84 are shown as being collimated to be within planes that pass through the axis 73. Other beam characteristics are contemplated such as, for instance, beams that are not centered on axis 72 or that include a fan breadth (i.e., fanning in the X-Y plane perpendicular to that illustrated in FIGS. 2 and 3). In fact, it is contemplated that, in embodiments that include a stationary CT collimator, the collimator would simply include two annular jaws that reside between the source and a facing surface of the detector array so that, in the X-Y plane, the fan beam is completely unblocked. In the alternative, where a rotatable collimator is provided, the rotatable collimator may include a second set of jaws that define edges to limit the fan beam in the X-Y plane. Both straight and curved collimator edges are contemplated.

One potential shortcoming of the system illustrated in FIGS. 2 and 3 that includes a fan beam source disposed to one side of detector ring 11 is that the area imageable via the source may be rather small due to the fan bean width at different depths through the region of interest. For instance, as best seen in FIG. 3, the beam width entering the illustrated patient is approximately half the width of the beam exiting the patient. While this problem can be partially dealt with by collecting data along conjugate trajectories (i.e., along opposite paths during 360° of source rotation), such a solution may require additional acquisition time and still leaves a relatively narrow acquisition width along the gantry axis 73.

Figure 4:
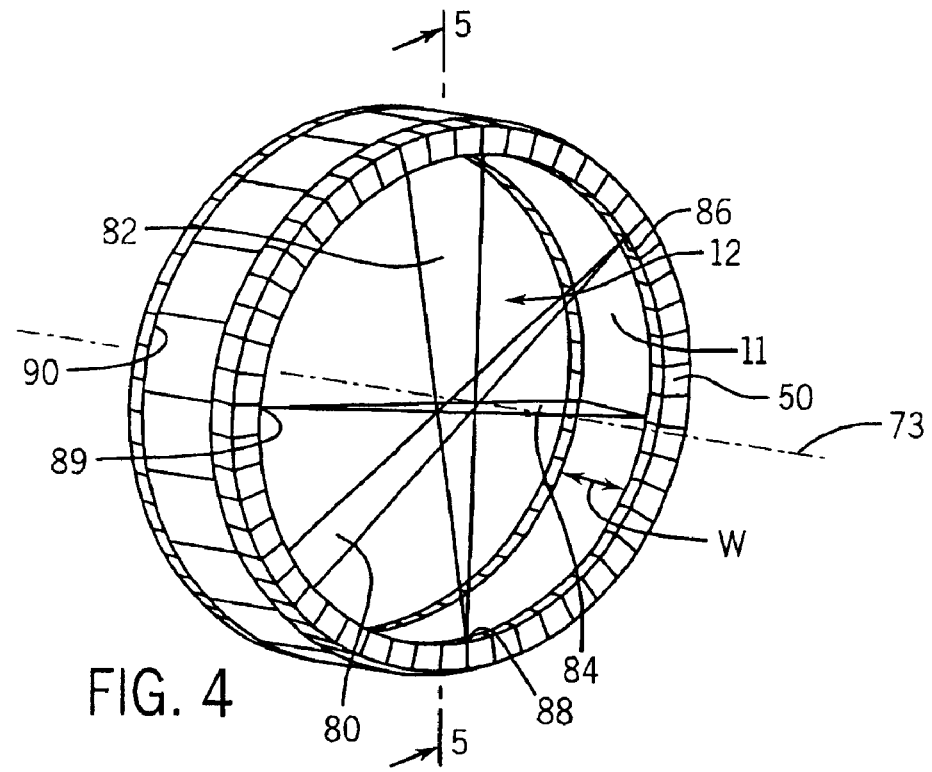
FIG. 4 is similar to FIG. 2, albeit illustrating a second embodiment of a detector ring and two separate annular X-ray sources that are separated by the detector ring.
Figure 5:
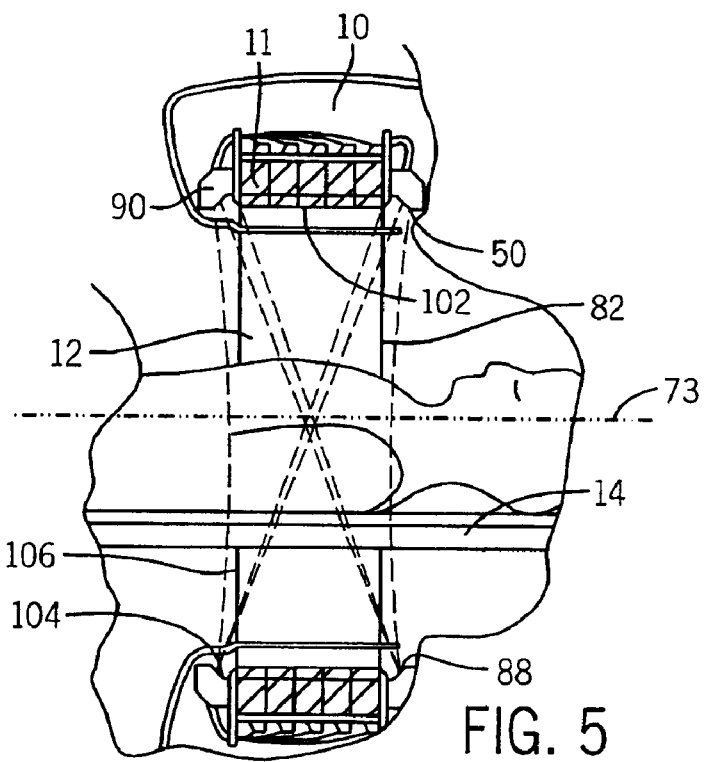
FIG. 5 is a view similar to FIG. 3 albeit corresponding to the line 5—5 of FIG. 4.

Referring now to FIGS. 4 and 5, a second embodiment of the invention is illustrated and includes two separate annular sources 50 and 90. Each of the sources illustrated in FIGS. 4 and 5 is similar to the source 50 described above and therefore will not be described again here in detail. As best seen in FIG. 5, source 90, like source 50, is controlled to generate an X-ray fan beam 106 that emanates from a selectable focal spot 104 and that is directed across the imaging area at an oppositely facing segment of detector ring 11. As illustrated in FIG. 5, by including two sources, X-rays can be transmitted along trajectories that pass through almost an entire region of interest so that larger regions are imageable during shorter periods of time.

When two sources 50, 90 are employed, one source on each side of ring 11, the fan beam trajectories have to be different for the two sources so that, when X-rays are detected by the ring segment opposite the sources, the source is known. Thus, for instance, looking into imaging space 12 along axis 73, source 50 may form a fan beam 82 along a first trajectory while source 90 forms a fan beam 84 along a second trajectory that is different then the first trajectory (see FIG. 4).

Referring again to FIGS. 1 through 3, detector rings 11 having various capabilities are contemplated and, based on those capabilities, various modes of system operation are contemplated. To this end, where ring 11 is capable of differentiating between different photon energy ranges corresponding to X-rays and annihilation photons, the source 50 may be operated in a pulse mode wherein the source 50 is turned on and off in rapid succession and along different trajectories. In this case, generally, it is assumed that all photons detected by ring segments instantaneously subtended by an X-ray fan beam when the source is on correspond to the source. While this assumption is not completely accurate (i.e., some of the collected photons are actually from annihilation events) the results are relatively accurate because, as well known in the industry, PET acquisition is relatively low count when compared to CT acquisition. In the alternative, some correction for acquired PET data may be implemented in software based on simultaneous events that occur in other detector ring segments. All ring 11 segments not subtended by a fan beam are employed in the conventional fashion to collect PET annihilation data.

In the alternative, where ring 11 is capable of distinguishing between annihilation photons (e.g., approximately 511 keV) and X-ray photons (e.g., <140 keV). True simultaneous CT-PET acquisition may be performed. In this case the entire detector ring 11 is used to collect annihilation range photons and the segments of ring 11 subtended by a CT X-ray source are used to collect both annihilation range and X-ray range photons and the sorter 69 in FIG. 1 is used to sort the data into respective data sets.

It should be understood that the methods and apparatuses described above are only exemplary and do not limit the scope of the invention, and that various modifications could be made by those skilled in the art that would fall under the scope of the invention. For instance, while there are several important advantages to using a solid-state ring detector like the one described above, sources (e.g., a rotating X-ray source) that resides outside but shoots across the imaging area are contemplated. As another instance, it is contemplated that the inventive system could be used in other fashions such as with dual energy CT where the CT data is binned into more than a single energy bin. Moreover, the PET processor 70 may operate, in some embodiments, prior to sorter 69, to identify likely PET events as the PET processor will reduce the number of potential events through coincidence detection. Furthermore, some embodiments may bin event energies between 511 keV and 140 keV to correct for PETA contamination of CT data.

To apprise the public of the scope of this invention, the following claims are made:

What is claimed is:

1. A photon imaging apparatus, the apparatus comprising: oppositely facing first and second emission/transmission detector segments disposed on opposite sides of an imaging area and defining the imaging area there between; and a radiation source disposed adjacent and outside the imaging area and adjacent at least one of the detector segments, the source generating a fan beam of radiation that emanates from a focal point and juxtaposed such that the fan beam is directed along a trajectory through the imaging area and toward the other of the detector segments; wherein the segments collect both emission and transmission radiation.

2. The apparatus of claim 1 further including a full ring detector assembly that, in addition to the first and second detector segments, includes a plurality of additional detector segments arranged about the imaging area to form an annular detector surface, the detector assembly having a detector width along a translation axis and the fan beam subtending the detector segment across the detector width.

3. The apparatus of claim 2 wherein the source is controllable to alter the position of the focal spot and hence the trajectory of the fan beam such that the fan beam is directable across the imaging area along various trajectories and toward various assembly segments.

4. The apparatus of claim 3 wherein the detector assembly simultaneously acquires both emission and transmission radiation and wherein the apparatus further includes a sorter linked to the detector that differentiates between collected emission and transmission radiation.

5. The apparatus of claim 3 wherein the source is turned on and off during data acquisition and wherein the detector segment subtended by the fan beam intermittently acquires emission and transmission data during the source off and source on periods, respectively.

6. The apparatus of claim 3 wherein the source includes a stationary annular source juxtaposed adjacent to and on a first side of the detector assembly.

7. The apparatus of claim 3 wherein the source simultaneously generates at least first and second fan beams from different focal spots and along different trajectories and toward different detector segments.

8. The apparatus of claim 3 wherein the source is a first source and the apparatus includes a second source juxtaposed on a second side of the detector assembly opposite the first side of the detector assembly, the second source assembly also generating a fan beam that is directed substantially across the imaging area at an opposing segment of the detector assembly.

9. The apparatus of claim 3 further including a source controller that controls the source to select various fan beam trajectories during a data acquisition session.

10. The apparatus of claim 1 wherein the source is a first source and the apparatus further includes a second source disposed adjacent and outside the imaging area and adjacent the other of the detector segments, the second source generating a second fan beam of radiation that emanates from a second focal point and juxtaposed such that the second fan beam is directed along a trajectory through the imaging area and toward the at least one of the detector segments.

11. A method for collecting both emission and transmission imaging data corresponding to a region of interest within a patient where a radio pharmaceutical has accumulated within the region of interest and is generating emission radiation, the method comprising the steps of: placing the region of interest within an imaging area between first and second photon detector segments; directing a fan beam of transmission radiation from a focal spot adjacent and outside the imaging area along a trajectory through the imaging area and toward at least one of the detector segments; and collecting both the emission and transmission radiation via the first and second detector segments.

12. The method of claim 11 wherein the step of placing includes placing the region of interest within an imaging area formed by an annular detector assembly having an annular detector surface wherein the detector assembly includes each of the first and second detector segments.

13. The method of claim 12 wherein the detector assembly has a detector width and wherein the step of directing a fan beam includes directing a beam that extends across the detector width.

14. The method of claim 13 further including the step of directing at least a second fan beam of transmission radiation across the imaging area and toward another detector segment that is different than the at least one detector segment.

15. The method of claim 11 further including modifying the focal spot position such that the fan beam trajectory is varied during data acquisition.

16. The method of claim 11 wherein the step of directing further includes pulsing the fan beam on and off and acquiring emission and transmission data during the source-off and the source-on periods, respectively.

17. The method of claim 11 wherein the step of collecting includes collecting the emission and transmission data simultaneously.

18. A combined emission-transmission imaging apparatus, the apparatus comprising: a full ring photon detector assembly including detector segments that are arranged to form an annular detector surface about an imaging area, and a radiation source disposed adjacent and outside the imaging area and adjacent a first side of the detector assembly, the source generating a fan beam of radiation that emanates from a focal point and juxtaposed such that the fan beam is directed along a trajectory through the imaging area and toward the detector surface on an opposite side of the imaging area, the source controllable to alter the position of the focal point and hence the trajectory of the fan beam such that the fan beam is directable across the imaging area along various trajectories and toward various segments of the detector surface; wherein the segments collect both emission and transmission radiation.

19. The apparatus of claim 18 wherein the source includes a stationary annular assembly juxtaposed adjacent to and on a first side of the detector assembly.

20. The apparatus of claim 19 wherein the source simultaneously generates at least first and second fan beams from different focal spots and along different trajectories and toward different detector segments.

* * * * *